United States Patent
Geisz et al.

(10) Patent No.: US 11,541,191 B2
(45) Date of Patent: Jan. 3, 2023

(54) DISTRIBUTED FLOW PATH INSUFFLATION

(71) Applicant: Lexion Medical, LLC, St. Paul, MN (US)

(72) Inventors: Carl M. Geisz, Edina, MN (US); Derrek W. Smith, Miami Beach, FL (US); Craig J. Cuta, Stillwater, MN (US)

(73) Assignee: LEXION MEDICAL, LLC, St. Paul, MN (US)

( * ) Notice: Subject to any disclaimer, the term of this patent is extended or adjusted under 35 U.S.C. 154(b) by 707 days.

(21) Appl. No.: 16/407,814

(22) Filed: May 9, 2019

(65) Prior Publication Data
US 2020/0353184 A1    Nov. 12, 2020

(51) Int. Cl.
*A61M 13/00* (2006.01)
*A61B 17/34* (2006.01)

(52) U.S. Cl.
CPC ....... *A61M 13/003* (2013.01); *A61B 17/3474* (2013.01); *A61M 2205/3331* (2013.01); *A61M 2205/50* (2013.01)

(58) Field of Classification Search
CPC ............ A61M 13/003; A61M 2205/50; A61M 2205/3331; A61M 2205/16; A61M 2205/3368; A61M 16/161; A61M 2205/3344; A61M 2204/334; A61M 2202/0007; A61B 17/3474; A61B 1/3132; A61B 17/3498; F16K 11/0853
See application file for complete search history.

(56) References Cited

U.S. PATENT DOCUMENTS

| | | | |
|---|---|---|---|
| 1,807,085 A * | 5/1931 | Crickmer | F16K 11/0853 137/625.47 |
| 4,207,887 A * | 6/1980 | Hiltebrandt | A61M 16/022 128/204.23 |
| 7,854,724 B2 * | 12/2010 | Stearns | A61B 17/3474 604/23 |

(Continued)

FOREIGN PATENT DOCUMENTS

WO    WO-2018039239 A1 *   3/2018   ........... A61B 1/3132

OTHER PUBLICATIONS

Mieszko Norbert Opilka, Zbigniew Lorenc and Jacek Starzewski (2011), Laparoscopic Access Techniques, Advanced Gynecologic Endoscopy, Dr. Atef Darwish (Ed.), ISBN: 978-953-307-348-4, InTech (www.intechopen.com/books/advanced-gynecologic-endoscopy/laparoscopic-access-techniques), 18 pages.

*Primary Examiner* — Bhisma Mehta
*Assistant Examiner* — Robert F Allen
(74) *Attorney, Agent, or Firm* — Baker Botts, LLP

(57) ABSTRACT

A system includes a bypass valve, a first conduit, and a second conduit. The bypass valve includes at least a first channel and a second channel and is configured to permit insufflation fluid to flow along a first flow path when the second channel is closed and permit the insufflation fluid to flow along a second flow path when the first channel is closed. The first conduit is coupled to the bypass valve and is configured to facilitate delivery of the insufflation fluid from an insufflator to the bypass valve. The second conduit is coupled to the first channel of the bypass valve and configured to facilitate delivery of the insufflation fluid from the bypass valve to the patient cavity via a first medical appliance.

9 Claims, 3 Drawing Sheets

(56) References Cited

U.S. PATENT DOCUMENTS

| | | | |
|---|---|---|---|
| 9,404,241 B1* | 8/2016 | Davantes | F16K 27/12 |
| 10,232,132 B2 | 3/2019 | Ott et al. | |
| 2006/0100579 A1* | 5/2006 | Maahs | A61M 13/003 |
| | | | 604/151 |
| 2016/0310077 A1* | 10/2016 | Hunter | A61B 5/0024 |
| 2017/0274160 A1* | 9/2017 | Mantell | A61M 39/24 |
| 2018/0055536 A1* | 3/2018 | Geisz | A61M 13/003 |

* cited by examiner

DISTRIBUTED FLOW PATH INSUFFLATION

TECHNICAL FIELD OF THE INVENTION

The present invention disclosure relates generally to medical procedures and more particularly to a method and system for insufflating a patient cavity using a distributed flow path.

BACKGROUND OF THE INVENTION

Providing an insufflation gas into a body cavity is referred to as insufflation. The purpose of insufflation is to inflate or distend the body cavity to allow a surgeon to explore a surgical site and/or otherwise provide a view of the site to be treated or observed. Insufflation is used in many common procedures including endoscopic surgical procedures, laparoscopic procedures performed on the abdominal cavity and orthoscopic procedures performed on the chest cavity. Additional medical access devices (e.g., trocars) can be used during the same surgical procedure to remove surgical smoke from the patient cavity or to continuously measure pressure within the body cavity.

As described in U.S. Pat. Nos. 5,411,474, 6,068,609, and 7,066,902 (incorporated by reference herein), insufflation gas is typically treated before being delivered to a patient cavity. Briefly, an insufflation gas is heated and hydrated (i.e., conditioned) before being directed, in some cases, by a trocar into a patient cavity. In order to hydrate the insufflation gas a charge of hydration fluid is typically injected into a device where the hydration fluid can humidify the insufflation gas and a heater can bring the insufflation gas to a temperature near body temperature. The conditioned insufflation gas is then delivered to a medical appliance (e.g., a trocar) for injection into a body cavity of a patient.

SUMMARY OF THE INVENTION

According to one embodiment, a system includes a bypass valve, a first conduit, and a second conduit. The bypass valve includes at least a first channel and a second channel, the first channel defining a portion of a first flow path for insufflation fluid and the second channel defining a first portion of a second flow path for the insufflation fluid. The bypass valve is configured to permit the insufflation fluid to flow along the first flow path when the second channel is closed and permit the insufflation fluid to flow along the second flow path when the first channel is closed. The first conduit is coupled to the bypass valve and is configured to facilitate delivery of the insufflation fluid from an insufflator to the bypass valve. The second conduit is coupled to the first channel of the bypass valve and is configured to facilitate delivery of the insufflation fluid from the bypass valve to the patient cavity via a first medical appliance.

According to another embodiment, a method for insufflating a body cavity with insufflation fluid includes determining, by an insufflator, a first pressure measurement indicative of a pressure of a patient cavity and supplying, by the insufflator, the insufflation fluid to the patient cavity based on the first pressure measurement, wherein the insufflation fluid is supplied according to a first setting which comprises at least a first volume and a first pressure. Supplying the insufflation fluid to the patient cavity includes directing the insufflation fluid through a first conduit to a bypass valve, the bypass valve including at least a first channel and a second channel defining a portion of a first flow path and first portion of a second flow path, respectively. Supplying the insufflation fluid to the patient cavity further includes directing the insufflation fluid to the patient cavity via the first flow path when the second channel is closed, wherein the first flow path is further defined by a second conduit coupling the first channel of the bypass valve to a first medical appliance, and directing the insufflation fluid to the patient cavity via the second flow path when the first channel is closed, wherein the second flow path is further defined by a second conduit coupling the second channel of the bypass valve to a second medical appliance According to yet another embodiment, a system includes an insufflator, a bypass valve, a first conduit, a second conduit, and a third conduit. The bypass valve includes at least a first channel and a second channel, the first channel defining a portion of a first flow path for the insufflation fluid and the second channel defining a portion of a second flow path for the insufflation fluid, wherein: the bypass valve is configured to permit the insufflation fluid to flow along the first flow path when the second channel is closed; and the bypass valve is configured to permit the insufflation fluid to flow along the second flow path when the first channel is closed. The first conduit is coupled to the bypass valve and configured to facilitate delivery of the insufflation fluid from the insufflator to the bypass valve. The second conduit is coupled to the first channel of the bypass valve and is configured to facilitate delivery of the insufflation fluid from the bypass valve to the patient cavity via a first medical appliance. The third conduit is coupled to the second channel of the bypass valve and is configured to facilitate delivery of the insufflation fluid from the bypass valve to the patient cavity via a second medical appliance.

The teachings of the disclosure provide one or more technical advantages. Embodiments of the disclosure may have none, some, or all of these advantages. For example, in some embodiments, a method allows for the continuous monitoring of pressure associated with a patient cavity during and after insufflation of the patient cavity. Continuous monitoring may result in decreased potential for physician harm resulting from insufflation fluid leakage and thus may also result in an increase in physician confidence while performing surgical procedures. As another example, a method provides for intelligent pressure monitoring wherein pressure sensors are automatically disabled when not in use. Thus, the intelligent pressure monitoring feature is associated with a reduction in power and computing resources. As yet another example, a method provides for the elimination of duplicate insufflation components (e.g., insufflator and conduits connecting to insufflation delivery device such as an insufflation needle or trocar). Other advantages will be apparent to those of skill in the art.

BRIEF DESCRIPTION OF THE DRAWINGS

For a more complete understanding of embodiments of the disclosure and the potential advantages thereof, reference is now made to the following written description taken in conjunction with the accompanying drawings, in which.

DETAILED DESCRIPTION OF THE INVENTION

Figure 1:
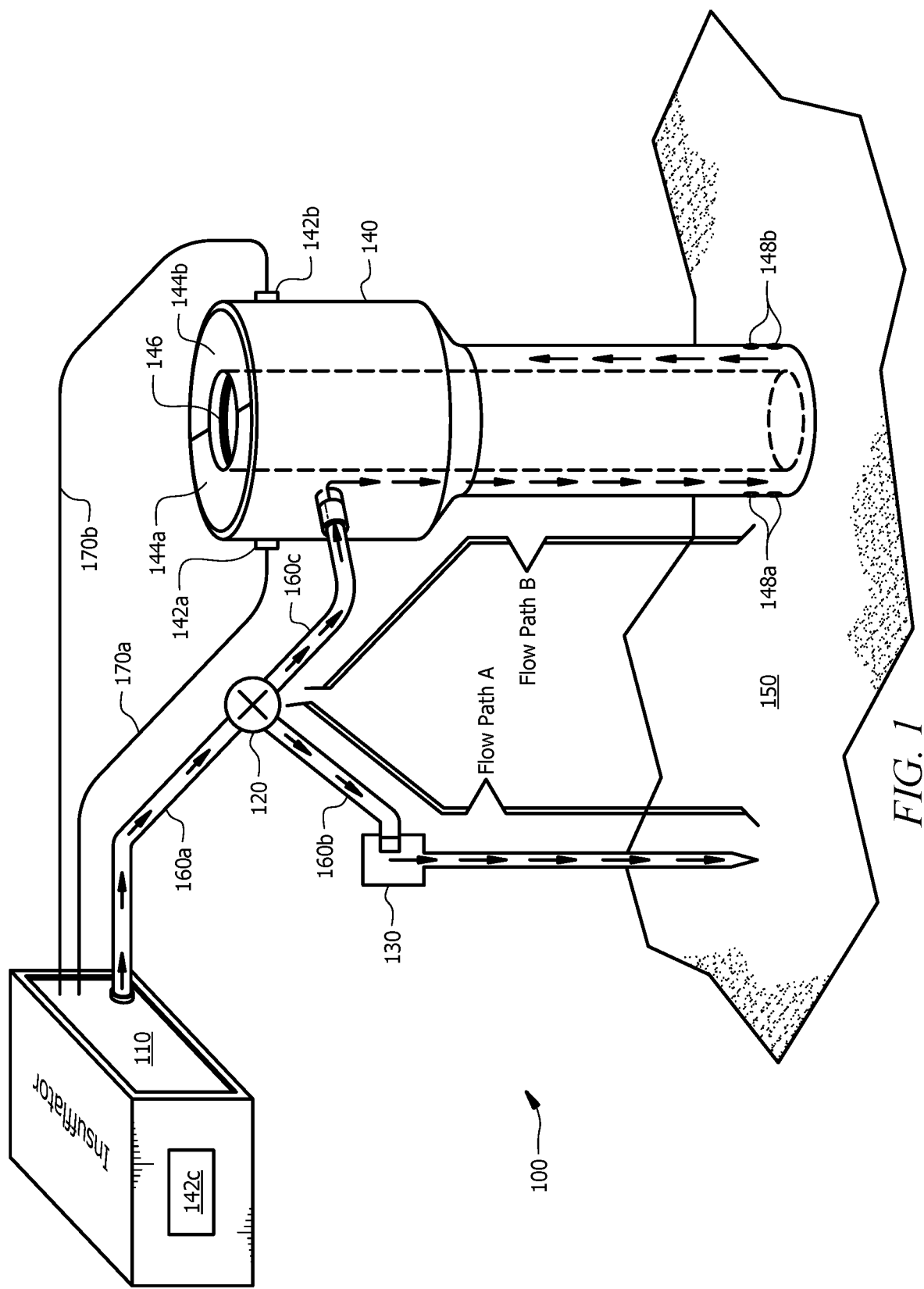
FIG. 1 illustrates an example of an insufflation system comprising an insufflator, a trocar, an insufflation needle, and a valve, according to certain embodiments of the present invention.

One of the requirements for delivery of insufflation gas to a patient's body cavity is to maintain the proper flow of insufflation gas into the body cavity. Normally, gas flows from a high-pressure gas source, which is remote from the patient, through an insufflation device and finally into a trocar where the gas is injected into the patient's body cavity. Typically, the insufflation gas is stored in high-pressure containers and a pressure regulator reduces the pressure of the gas to a lower pressure. The low pressure gas is typically delivered to the trocar through an insufflation device containing a set of inline end connectors that couple the source of insufflation gas, the pressure regulator, the filter, the heater, the hydrator, and the trocar to each other. Typically, before being delivered to the patient cavity, the insufflation gas is conditioned by filtering, heating and/or hydrating. The insufflation gas may flow through any suitable number of inline end connectors, which are typically connected by flexible tubing (also referred to herein as conduits), before being delivered to the patient cavity.

In some cases, physicians or other medical practitioners may prefer to deliver insufflation gas to patient cavity in two phases, first using a first medical appliance (e.g., an insufflation needle) and thereafter using second medical appliance (e.g., a trocar). Delivering insufflation gas via two different medical appliances may be preferred because one medical appliance may have a smaller profile than the other.

Conventional two-phase insufflation may be associated with various drawbacks. As one example, one conventional solution requires two sets of insufflation components (e.g., insufflator, conduits); one set to be used with the first medical appliance and the other set to be used with the second medical appliance.

Applicant has previously described and patented a solution that addresses and eliminates the need for insufflating using duplicative insufflation components. See U.S. Pat. No. 10,232,132 ("the '132 Patent") (incorporated by reference herein). The '132 Patent generally describes a two-stage insufflation method using a trocar-adaptor-needle assembly (i.e., coupling, using an adaptor, a trocar cannula to an insufflation needle). At the first stage of the insufflation method, insufflation fluid is delivered through the trocar-adaptor-needle assembly; at the second stage of the insufflation method, insufflation fluid is delivered directly through the trocar cannula. Transition from the first stage of the insufflation method to the second stage of the insufflation method requires disconnection of the adaptor and needle from the trocar-adaptor-needle assembly. Although such adaptor eliminates the need for duplicative insufflation components, such delivery method is not a perfect solution. Notably, disconnection of the adaptor and needle from trocar-adaptor-needle assembly requires the removal of the trocar-adaptor-needle from the patient cavity. In the period of time that it takes to remove the trocar-adaptor-needle assembly, modify the trocar-adaptor-needle assembly, and thereafter position and insert the trocar in the patient cavity, leakage of the insufflation fluid may occur. Any leakage of the insufflation fluid results in deflation of the patient cavity and therefore diminishes the physician's view of the site of interest. As will be recognized by those of skill in the art, inserting a trocar into a patient cavity that is not sufficiently inflated is risky as the trocar may pierce or otherwise damage organs surrounding the site of interest.

Other conventional two-phase insufflation solutions also experience the same leakage risk due to disconnection and reconnection of components. For example, a popular two-phase insufflation solution involves initially insufflating using a first medical appliance (e.g., an insufflation needle) connected to a conduit, that is in turn connected to the insufflator. Once the patient cavity is sufficiently insufflated using the first medical appliance, the conduit is disconnected from the first medical appliance and connected to a second medical appliance (e.g., a trocar). As one of ordinary skill in the art will recognize, disconnection and reconnection of the conduit to the first and second medical appliance, respectively, presents an opportunity for insufflation gas leakage and therefore also poses an increased risk of the medical procedure to the patient.

The present disclosure describes an insufflation system and method that overcomes the shortcomings of the conventional insufflation solutions described above. In particular, the present disclosure describes an insufflation system and method that operates using a single set of insufflation components and reduces or eliminates leakage of insufflation gas during the insufflation process, in one embodiment. The insufflation system and method described herein also contemplates intelligent pressure monitoring which provides various efficiencies with respect to time and computing resources. Example embodiments are best understood by referring to FIGS. 1 through 4 of the drawings and the description below, like numerals being used for like and corresponding parts of the various drawings.

FIG. 1 is a schematic diagram of an insufflation system 100. In some embodiments, insufflation system 100 includes an insufflator 110, conduits (e.g., 160a, 160b, 160c), a valve 120, and one or more medical appliances. In the embodiment illustrated in FIG. 1, insufflation system 100 includes a first medical appliance (i.e., insufflation needle 130) and a second medical appliance (i.e., trocar 140). Other embodiments of insufflation system 100 may include other medical appliances. For example, in another embodiment, both the first and second medical appliances are trocars, the first medical appliance being a hasson trocar. As will be recognized by one of ordinary skill, system 100 may include one or more additional components. As an example, system 100 may further include a controller that controls the operation of one or more components of FIG. 1. This disclosure describes and depicts an example of such controller with respect to FIG. 4.

Generally, FIG. 1 shows the distal end of insufflation needle 130 and trocar 140 positioned within the abdominal cavity 150 of a patient. In general, insufflator 110 supplies insufflation gas to patient cavity 150. The insufflation gas is directed from insufflator to valve 120 via conduit 160a and is thereafter directed to patient cavity 150 via at least one flow path. FIG. 1 illustrates two flow paths: the first flow path, identified in FIG. 1 as "Flow Path A," includes conduit 160b and insufflation needle 130; the second flow path, identified in FIG. 1 as "Flow Path B," includes conduit 160c and trocar 140. As will be described in further detail below, valve 120 is configured to direct the insufflation gas to at least one of Flow Path A or Flow Path B. In addition to providing a flow path for insufflation gas, trocar 140 permits the insertion of a surgical instrument (not illustrated) into patient cavity 150. In the embodiment illustrated in FIG. 1, a physician or other medical practitioner can insert a surgical instrument through an inner tubular lumen 146 of trocar 140 in order to access patient cavity 150 with the surgical instrument.

System 100 may further include one or more sensors (e.g., 142a, 142b, 142c). Sensors (e.g., 142a, 142b, 142c) are configured to measure a variable (e.g., pressure, humidity, temperature) and are, in some embodiments, of system insufflator coupled to communicatively coupled to other components 100 (e.g., controller of system 100, 110). Sensors (e.g., 142a, 142b, 142c) may be communicatively components of system 100 via a wired or wireless connection. As illustrated in FIG. 1, sensors 142a and 142b communicate with insufflator 110 via cables 170a and 170b, respectively. Communications between sensors (e.g., 142a, 142b, 142c) and components of system 100 may include instructing a sensor (e.g., 142a, 142b, 142c) to take a measurement, such sensor (e.g., 142a, 142b, 142c) reporting a measurement, and instructing insufflator 110 to supply insufflation gas under specified conditions (e.g., at a particular pressure and/or volume).

As illustrated in FIG. 1, system 100 includes three sensors: sensors 142a, 142b, and 142c. Sensor 142a may be configured to (1) measure a humidity and/or temperature of the insufflation gas as it flows through trocar 140; and (2) communicate such measurement(s) to insufflator 110 and/or a controller of insufflation system 100. Sensors 142b and 142c may be configured to (1) measure a pressure corresponding to patient cavity 150; and (2) communicate such measurement to insufflator 110 and/or a controller of insufflation system 100. As will be described in further detail below, sensor 142b may measure a pressure corresponding to patient cavity 150 through an outer tubular lumen 144a, 144b of trocar 140 and sensor 142c may measure a pressure corresponding to patient cavity 150 through Flow Path B. Although this disclosure describes and depicts only three sensors (i.e., 142a, 142b, 142c), this disclosure contemplates system 100 including any appropriate number of sensors.

Sensors 142 may sense pressure or a change in pressure. Sensor 142 may measure absolute pressure or a pressure relative to some other pressure. In some embodiments, sensor 142 is an absolute sensor that can measure pressure in patient cavity 150 (if disposed within patient cavity 150) or in the room in which the associated operation is taking place. In particular embodiments, sensor 142 can measure absolute barometric pressures with an accuracy of less than 1 Pascal pressure and therefore have the ability to measure the relative changes in altitude of close to one inch. Such pressure sensors are readily available in the marketplace. Insufflator 110 of system 100 may be any suitable source of insufflation gas at any suitable pressure and may include a pressurized gas source. Insufflator 110 may adjust the supply of insufflation gas to patient cavity 150 by adjusting the pressure and/or the volume of insufflation gas supplied to patient cavity 150. As described above, insufflator 110 may supply insufflation gas to patient cavity 150 based on one or more pressure measurements (e.g., pressure measurements taken by sensors 142b and/or 142c). The insufflation gas may be any suitable gas used for insufflation purposes. As one example, insufflation gas may be carbon dioxide.

Insufflator 110 may include any appropriate hardware and/or software for processing signals indicative of insufflation gas measurements and processing such signals to convert them into useful information, such as converting them into pressures, heights, and/or other data that can be used control the flow of insufflation gas to patient cavity 150, and further for processing such data to determine a desired pressure and/or volume of insufflation gas supplied to patient cavity 150 and for effecting such delivery. Accordingly, insufflator 110 may include at least one processor, a computer-readable medium to store instructions, and at least one communication interface for receiving and sending information. In some embodiments, insufflator 110 includes a controller such as the controller 400 described and depicted in FIG. 4.

Figure 2:
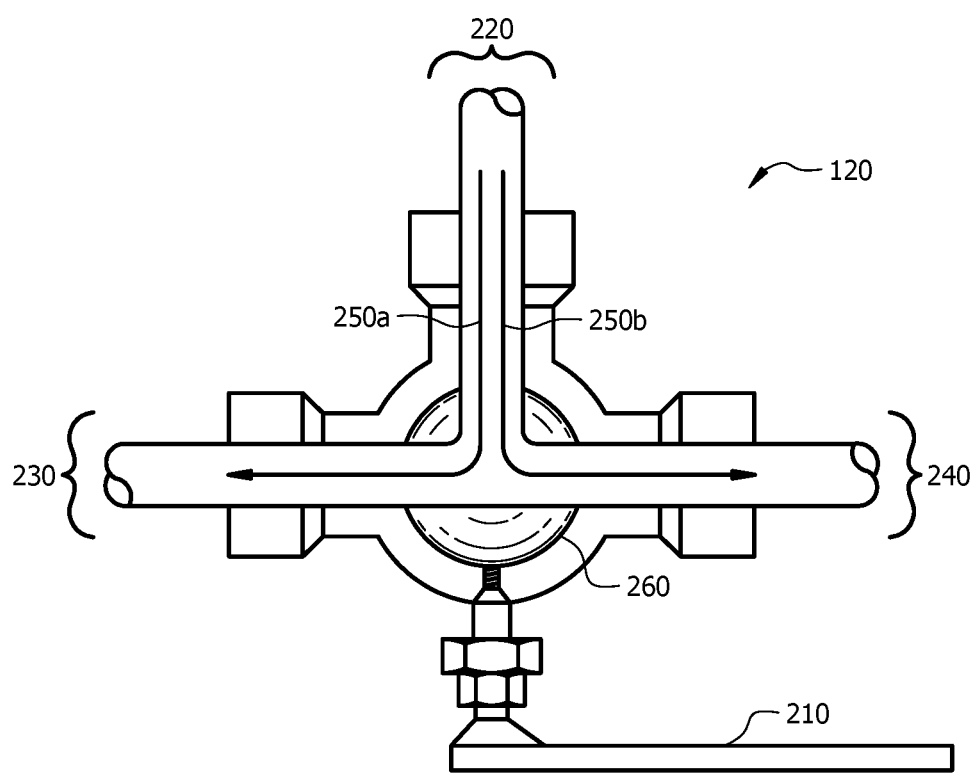
FIG. 2 illustrates the valve of the system of FIG. 1, according to certain embodiments of the present invention.

As described above, system 100 includes valve 120. Valve 120 may be any suitable device configured to direct insufflation gas along two or more flow paths. As illustrated in FIGS. 1 & 2, valve 120 is configured to discharge insufflation gas to one of two flow paths: Flow Path A and Flow Path B. Insufflation gas carried via Flow Path A is discharged from valve 120 to conduit 160b and is thereafter directed through a first medical appliance (e.g., insufflation needle 130) to patient cavity 150. In contrast, insufflation gas carried via Flow Path B is discharged from valve 120 to conduit 160c and is thereafter directed through a second medical appliance (e.g., trocar 140) to patient cavity 150. Valve 120 is further described in reference to FIG. 2.

As described above, conduits 160a-c may direct the flow of insufflation gas between components of system 100. In some embodiments, conduits 160a-c couple to ports located on such components. For example, as illustrated in FIG. 1, conduit 160a is coupled on one end to a port corresponding to insufflator 110 and is coupled on the opposite end to a port corresponding to valve 120. As another example, conduit 160b is coupled on one end to a port corresponding to valve 120 and is coupled on the opposite end to a port corresponding to insufflation needle 130. As yet another example, conduit 160c is coupled on one end to a port corresponding to valve 120 and is coupled on the opposite end to a port corresponding to trocar 140.

Conduits 160a-c may comprise any suitable material that facilitates the transport of insufflation gas. As an example, conduits 160a-c may comprise flexible PVC tubing. In some embodiments, in addition to providing a pathway for transporting insufflation gas, conduits 160a-c provide a pathway for taking pressure measurements. As an example, sensor 142c may take a pressure measurement indicative of a pressure of patient cavity 150 via conduits 160a and 160b. As will be understood by one of ordinary skill in the art, pressure measurements indicative of the pressure of body cavity 150 may be taken via Flow Path A when insufflator 110 is not supplying insufflation gas. Although system 100 is described and depicted as having only three conduits (i.e., 160a, 160b, 160c), this disclosure contemplates system 100 including any suitable number of conduits.

As described above, system 100 includes trocar 140. Although system 100 is described and depicted as only having a single trocar (trocar 140), this disclosure contemplates system 100 including any suitable number of trocars 140. Trocar 140 may be any suitable trocar through which insufflation gas may be supplied to a patient cavity. Examples of one or more trocars are provided in U.S. Pat. No. 8,715,219 (the '219 Patent), U.S. Pat. No. 7,285,112 (the '112 Patent), and U.S. Pat. No. 8,216,189 (the '189 Patent), which are hereby incorporated by reference as if fully set forth herein. Trocar 140 may have a single lumen or may be formed with an inner tubular lumen and an outer tubular lumen such that insufflation gas may be supplied through one of the lumens but not the other. Further, any of the lumens may be divided into multiple, separate chambers, such that gas in one chamber does not enter the other chamber. Examples of the above multiple lumens and multiple chambered trocars are described in U.S. application Ser. No. 14/792,873, entitled "Method and System for Gas Maintenance to a Body Cavity Using a Trocar," which is hereby incorporated by reference. Trocar may be open or closed at the distal end, as the application of the trocar would allow.

As illustrated in FIG. 1, trocar 140 includes an outer tubular lumen (e.g., 144a, 144b) disposed about an inner tubular lumen 146. Medical instruments (e.g., scope, grasper, scissors) may be inserted through inner tubular lumen 146 of trocar 140 in order to access the site of interest within body cavity 150.

In some embodiments, outer tubular lumen (e.g., 144a, 144b) is divided into two or more chambers (e.g., chamber 144a and chamber 144b). The division of outer tubular lumen (e.g., 144a, 144b) into separate chambers may provide benefits which will be recognized by one of ordinary skill in the art. As an example, by dividing outer tubular lumen (e.g., 144a, 144b) into two or more chambers, trocar 140 can deliver insufflation gas to patient cavity 150 while also measuring a pressure (e.g., using sensor 142) indicative of a pressure of patient cavity 150. As shown in FIG. 1, conduit 160c directs insufflation gas to chamber 144a of trocar 140 where it is thereafter directed, via apertures 148a, to patient cavity 150. As is also shown in FIG. 1, apertures 148b provide a path into chamber 144b of trocar 140 in which sensor 142b may take a pressure measurement indicative of a pressure of patient cavity 150. Although trocar 140 is depicted in FIG. 1 as having two apertures 148a and two aperture 148b, this disclosure recognizes that trocar 140 may include any suitable number of apertures 148a and 148b.

As described above, trocar 140 may include any suitable number of sensors 142, one or more of which may be capable of taking pressure measurements. Sensors 142 may be located anywhere in, on, or through trocar 140. In some embodiments, sensors 142 are located on the exterior of trocar 140 such that changes of pressure within trocar 140 (e.g., due to the supply of insufflation gas to patient cavity 150) do not affect the pressure measured by sensor 142. As described above, sensors 142 may be absolute pressure sensors that can measure pressure in patient cavity 150 (if disposed within patient cavity 150) or in the room in which the associated operation is taking place.

Sensors 142 may be coupled to components of system 100 through any suitable technique, including a wireless or a wired connection (e.g., cables 170a and 170b). Sensor 142 supplies pressure data to a controller of system 100, which may be comprised within insufflator 110. In such an embodiment, insufflator 110 uses this pressure data to control the supply on insufflation gas by insufflator 110. In particular embodiments, this may include determining the change in height of trocar 140 relative to changes in cavity pressure and thus the resulting change in height of patient cavity 150, as described in greater detail in co-pending application Ser. No. 15/293,013 entitled Method and System for Controlling Pressurization of a Patient Cavity Using Cavity Distension Measured by a Pressure Sensor of a Trocar incorporated herein by reference.

Generally, system 100 is used to insufflate patient cavity 150. Upon coupling conduits (e.g., 160a, 160b, 160c) to components of system 100 as illustrated in FIG. 1, insufflation may begin. In some embodiments, insufflation needle 130 and trocar 140 are inserted into patient cavity 150 and valve 120 is opened such that insufflation gas can be delivered via Flow Path A. Insufflator 110 may then be turned on such that insufflation gas is delivered to patient cavity 150 via Flow Path A. Before and/or during insufflation, one or more measurements are taken by sensors 142 and relayed to insufflator 110 as described above. As is also described above, insufflator 110 supplies insufflation gas to patient cavity 150 based on measurements taken by sensors 142. Once patient cavity 150 has been insufflated to desired levels (e.g., 15 mmHg), valve 120 is adjusted to permit the flow of insufflation gas along Flow Path B such that insufflation gas is delivered to patient cavity 150 through trocar 140.

This disclosure recognizes that each component of system 100 does not need to be coupled in order to begin insufflation. As an example, insufflation gas may be delivered along Flow Path A without first coupling conduit 160c to trocar 140. To ensure efficiency benefits, conduit 160c is coupled to valve 120 and trocar 140 before valve 120 is adjusted to permit insufflation fluid to flow along Flow Path B. In other words, system 100 may be assembled during or after use of one or more components of system 100.

Furthermore, system 100 may be disassembled during or after use of one or more components of system 100. For example, upon insufflating patient cavity 150 with insufflation needle 130 and adjusting valve 120 to prevent insufflation gas from flowing along Flow Path A (or otherwise permit the flow of insufflation gas along Flow Path B), conduit 160b and insufflation needle 130 may be removed from system 100.

Figure 3:
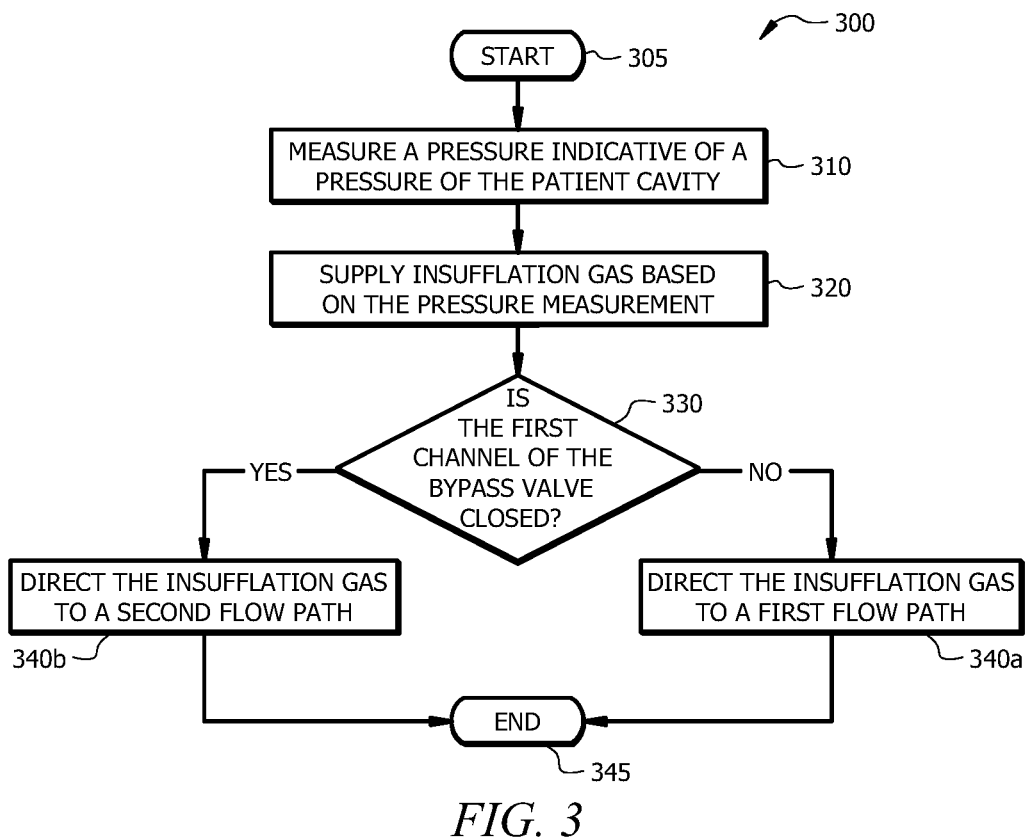
FIG. 3 is a flow chart illustrating a method of insufflating a patient cavity using the valve of FIG. 2, according to one embodiment of the present invention.

This disclosure describes valve 120 in further detail with respect to FIG. 2 and describes certain methods of insufflating a patient cavity with respect to FIG. 3. Finally, this disclosure describes details of a controller of system 100 with respect to FIG. 4.

FIG. 2 illustrates one embodiment of valve 120. As shown in FIG. 2, valve 120 is a ball valve that provides multiple flow paths. Although this disclosure describes and depicts valve 120 as a ball valve, this disclosure recognizes that valve 120 may be any suitable type of valve 120 that provides multiple flow paths for insufflation gas. For the avoidance of doubt, this disclosure recognizes valve 120 being any suitable solenoid or pneumatic valve.

As illustrated in FIG. 2, valve 120 includes handle 210, inlet 220, a first outlet 230, a second outlet 240, and a ball 260. Generally, ball 260 is rotated within valve 120 based on movements of handle 210. One or more channels (e.g., 250a and 250b) within valve 120 may be opened as ball 260 rotates within valve 120. As one example, turning handle 210 90° may open channel 250a and close channel 250b. As a result of turning handle 210 90°, insufflation gas may be permitted to flow into inlet 220 and out of valve 120 via outlet 230. As another example, turning handle 210 180° may open channel 250b and close channel 250a. As a result of turning handle 210 180°, insufflation gas may be permitted to flow into inlet 220 and out of valve 120 via outlet 240. As yet another example, turning handle 210 270° may close two or more channels 250 (e.g., 250a and 250b) such that insufflation gas cannot flow along Flow Path A or Flow Path B (or insufflation gas is otherwise blocked from flowing into inlet 220 of valve 120). In some embodiments, turning handle 210 360° may open two or more channels 250 (e.g., 250a and 250b) such that insufflation gas is permitted to flow along Flow Path A and Flow Path B. Although this disclosure describes various settings for valve 120, this disclosure contemplates valve 120 including any desirable valve setting that permits insufflation gas to flow (or not flow) through one or more components of system 100.

In some embodiments, conduit 160a is coupled to inlet 220 to permit the flow of insufflation gas from insufflator 110 to valve 120. In some embodiments, conduit 160b is coupled to outlet 230 to permit the flow of insufflation gas along Flow Path A and conduit 160c is coupled to outlet 240 to permit the flow of insufflation gas along Flow Path B. Accordingly, this disclosure recognizes that turning handle 210 may permit insufflation gas to flow along Flow Path A and/or Flow Path B.

In some embodiments, valve 120 does not include handle 210 to control actuation of ball 260. Instead, ball 260 (or other suitable valve mechanism for blocking, or otherwise closing, channels (e.g., 250a and 250b)) may actuate based on receipt of instructions from a controller (e.g., controller 400 of FIG. 4). As described above, controller may be comprised within insufflator 110. In other embodiments, such controller may be external to insufflator 110. In some embodiments, controller is programmed to actuate ball 260 (or other suitable valve mechanism for blocking, or otherwise closing, channels (e.g., 250a and 250b)) in a manner that closes one flow path (e.g., Flow Path A) and opens another flow path (e.g., Flow Path B) in response to determining that desired levels of insufflation gas have been attained (e.g., when patient cavity 150 has been insufflated to 15 mmHg). In this manner, insufflation gas may be continuously delivered to patient cavity 150 even though the flow path for the insufflation gas has changed. As will be recognized by one or ordinary skill, continuous flow of insufflation gas may result in certain benefits relative to conventional insufflation system, including reducing or eliminating leakage of insufflation gas.

FIG. 3 is a flow chart illustrating a method 300 of insufflating a patient cavity using system 100. The method may utilize structural items such as those described in FIGS. 1 through 2 or may use alternative structural items. Computational steps described below may be performed by any suitable computation device, including a controller that may or may not be a subcomponent of insufflator 110.

The method 300 begins at step 305 and continues to step 310. At step 310, system 100 measures a pressure indicative of a pressure of patient cavity 150. In some embodiments, the pressure measurement taken at step 310 is measured by one or more sensors 142. As described above, sensors 142 may be located in, on, or through trocar 140 and/or insufflator 110. In some embodiments, sensors 142 may continuously measure a pressure within patient cavity 150 and communicate a signal indicative of the measurement(s) to the controller of system 100.

Figure 4:
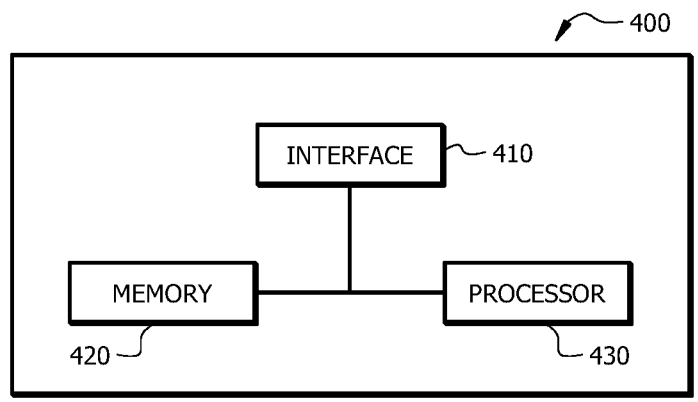
FIG. 4 illustrates an example controller operable to control one or more components of system 100, including the insufflator of FIG. 1.

In some embodiments, one or more pressure measurements are taken by sensor 142b and communicated to a controller (e.g., controller 400 of FIG. 4. In such embodiment, gas may enter into outer chamber 144b of trocar 140 through apertures 148b so that the pressure of the gas may be measured by sensor 142b. In other embodiments, one or more pressure measurements are taken by sensor 142c collocated with insufflator 110. As will be recognized by those of ordinary skill, to ensure the accuracy of the reading, pressure measurements using sensor 142c should occur when insufflator 110 is not supplying insufflation gas to patient cavity 150. Although this disclosure describes and depicts particular positions in system 100 for sensors 142, this disclosure recognizes that sensors 142 may be located in any suitable position that would permit sensors 142 to measure pressure indicative of a pressure of patient cavity 150. Once system 100 determines such pressure measurement(s), the method 300 may proceed to step 320.

At step 320, system 100 supplies insufflation gas to patient cavity 150 based on the pressure measurement taken at step 310. As an example, if controller receives a pressure measurement at step 310 of 15 mmHg, controller may instruct insufflator 110 to supply 1 L/min of insufflation gas to patient cavity. This disclosure recognizes that variables other than the pressure of insufflation gas may also be monitored and adjusted while delivering insufflation gas using system 100. As an example, sensor 142a may be configured to sense humidity and/or temperature information which is relayed to a controller that thereafter instructs insufflator 110 to adjust the humidity and/or temperature of the supply of insufflation gas. Once insufflation gas has been supplied to patient cavity 150, the method 300 may proceed to decision step 330.

At decision step 330, system 100 determines whether first channel 250a is open (not blocked) or closed (blocked). If at step 330, system 100 determines that first channel 250a is open, the method 300 proceeds to a step 340a. If at step 330, system 100 instead determines that first channel 250a is closed, the method 300 proceeds to a step 340b.

At step 340a, system 100 directs the insufflation gas to a first flow path (e.g., Flow Path A of FIG. 1). At step 340b, system 100 directs the insufflation gas to a second flow path (e.g., Flow Path B of FIG. 1). As discussed above, it may be preferable to initially deliver insufflation gas via a first flow path and thereafter deliver insufflation gas via a second flow path. As described above, channels (e.g., 250a and 250b) of valve 120 may be opened or closed manually (e.g., by turning handle 210) and/or based on instructions provided by the controller of system 100 (e.g., controller 400). To deliver insufflation gas initially through insufflation needle 130 of system 100, channel 250a should be opened and channel 250b should be closed. Once channels (e.g., 250a and 250b) are positioned as desired, insufflator 110 may discharge insufflation gas to valve 120 via conduit 160a and can thereafter be directed to insufflation needle 130 via conduit 160b (Flow Path A). In some embodiments, the method 300 proceeds to an end step 345 once insufflation gas has been directed to either the first or second flow path.

Modifications, additions, or omissions may be made to the methods described herein without departing from the scope of the disclosure. The methods may include more, fewer, or other steps. Additionally, steps may be performed in any suitable order. As an example alternative method, the method 300 may continue to a step whereby it is determined that patient cavity 150 is insufflated to a desired level (15 mmHg). Upon determining that the desired level has been reached, channel 250a may be closed and channel 250b may be opened such that insufflation gas can be delivered along Flow Path B (rather than Flow Path A). In some embodiments, this transition may be performed automatically. For example, upon determining that patient cavity has a pressure of 15 mmHg, controller may instruct ball 260 (or other suitable valve mechanism for blocking, or otherwise closing, channels (e.g., 250a and 250b)) to rotate such that channel 250a is closed and channel 250b is open.

Additionally, system 100 may also be configured to implement certain functionalities in response to determining that one or more channels (e.g., 250a and 250b) of valve 120 are closed. As an example, system 100 may automatically adjust the operational settings of insufflator 110 in response to determining that one channel (e.g., 250b) has been opened and another channel (e.g., 250a) has been closed. In such example, insufflator may receive instructions to adjust the volume and/or pressure of the insufflation gas being supplied in order to ensure that the pressure of patient cavity 150 is maintained in response to a controller of system 100 determining that channel 250a is closed. As another example, system 100 may automatically disable one or more sensors 142 from taking measurements (e.g., pressure measurements) in response to determining that one channel (e.g., 250a) has been opened and another channel (e.g., 250b) has been closed. As yet another example, in response to determining that two or more channels (e.g., 250*a* and 250*b*) are closed (e.g., based on pressure measurements indicative of the pressure of patient cavity 150), insufflator 110 may display, on insufflator 110, a message indicating such (e.g., insufflator 110 may display "OCCLUSION" or "ERROR"), In some embodiments, adjusting operational settings of system components (e.g., sensors 142, insufflator 110) may result in efficiency and/or timing benefits.

In some embodiments, controller of system 100 determines that one or more channels (e.g., 250*a* and 250*b*) are closed based on a rapid pressure rate rise/decline. For example, controller may determine that channel 250*a* and/or 250*b* is closed by determining that the pressure within patient cavity 150 increased or decreased by 5 mmHG within 1 seconds.

Although this disclosure identifies particular ways of identifying whether channel (e.g., 250*a* and 250*b*) is open or closed, this disclosure recognizes that identifying whether channel (e.g., 250*a* and 250*b*) is open or closed may be determined in any suitable way.

Method 300 may also include one or more of the following steps: (1) determine that a first sensor 142 is providing inaccurate or unreliable pressure readings; and (2) to instruct insufflator 110 to supply insufflation gas based on measurements determined by a second sensor 142. In some embodiments, controller of system 100 is responsible for performing these steps. In some embodiments, controller of system 100 analyzes pressure measurement(s) received from a first sensor 142 for indications of whether the signals are indicative of the measured pressure being inaccurate or otherwise suggesting that first sensor 142 is operating in a less than optimal manner. Any suitable factors may be considered in such analysis; however, certain factors that may indicate first sensor 142 is operating in a less than optimal manner include (1) whether the received signal is not within an expected range for the received signal; (2) whether error data is received, such as whether errors have occurred due to interference from a power signal, the wrong number of bits have been received, data is received in the wrong format, or data is received with improper spacing (3) whether proper acknowledgment bits are not received from the primary pressure sensor, (4) whether the received signal is not within an expected voltage range, (5) whether expected new updated status bits are not received, such as whether a signal has changed enough to indicate a new measurement has occurred as opposed to a signal being so close to a previous signal to indicate no new measurement has occurred; and (6) in the case where system 100 includes two or more pressure sensors 142, whether measurements by the two or more sensors 142 are not within a certain range of each other. Upon determining that first sensor 142 is providing inaccurate or unreliable pressure readings, controller of system 100 may instruct insufflator 110 to supply insufflation gas based on pressure readings from a second sensor 142. In some embodiments, first sensor 142 is disabled upon determining that first sensor 142 is providing inaccurate or unreliable pressure readings. In other embodiments, pressure readings from first sensor 142 are ignored upon determining that first sensor 142 is providing inaccurate or unreliable pressure readings.

The method 300 may also include one or more disassembly steps wherein components may be removed from system 100 (e.g., insufflation needle 130 and/or conduit 160*b*) although insufflation gas continues to be delivered to patient cavity 150 (e.g., via conduit 160*c* and trocar 140).

Although this disclosure describes and depicts particular embodiments of the present invention, it will be understood that various substitutions and alterations can be made therein without departing from the spirit and scope of the present invention, as defined by the following claims. For example, although sensors 142 have been described above as being located on trocar 140 and/or insufflator 110, sensor 142 may also be located on, in, or through other medical appliances as well. Such medical appliances may be or include one of: a needle, a stapler, a grasper, a pair of scissors, a scalpel, a cutter, an electrode, an end seal, a probe, a multiple access port, and a single access port. Although this disclosure identifies certain types of medical appliances (including trocars 140), this disclosure recognizes that sensor 142 may be located on, in, or through any suitable medical appliance. For example, this disclosure recognizes any medical appliance that can puncture the skin as a medical appliance.

FIG. 4 illustrates an example controller 400 of system 100, according to certain embodiments of the present invention. As described above, controller may be internal or external to one or more components of system 100. In a particular embodiment, controller is comprised within insufflator 110. Controller 400 may comprise one or more interfaces 410, memory 420, and one or more processors 430. Interface 410 receives input (e.g., sensor data, user input), sends output (e.g., instructions), processes the input and/or output, and/or performs other suitable operation. Interface 410 may comprise hardware and/or software.

Processor 430 may include any suitable combination of hardware and software implemented in one or more modules to execute instructions and manipulate data to perform some or all of the described functions of controller 400. In some embodiments, processor 430 may include, for example, one or more computers, one or more central processing units (CPUs), one or more microprocessors, one or more applications, one or more application specific integrated circuits (ASICs), one or more field programmable gate arrays (FPGAs), and/or other logic.

Memory (or memory unit) 420 stores information. Memory 420 may comprise one or more non-transitory, tangible, computer-readable, and/or computer-executable storage media. Examples of memory 420 include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable medium.

Modifications, additions, or omissions may be made to the systems, apparatuses, and methods described herein without departing from the scope of the disclosure. The components of the systems and apparatuses may be integrated or separated. Moreover, the operations of the systems and apparatuses may be performed by more, fewer, or other components. One skilled in the art will also understand that the system contemplated by this disclosure can include other components that are not illustrated but are typically included with such systems. Additionally, operations of the systems and apparatuses may be performed using any suitable logic comprising software, hardware, and/or other logic. As used in this document, "each" refers to each member of a set or each member of a subset of a set.

Although this disclosure has been described in terms of certain embodiments, alterations and permutations of the embodiments will be apparent to those skilled in the art. Accordingly, the above description of the embodiments does not constrain this disclosure. Other changes, substitutions, and alterations are possible without departing from the spirit and scope of this disclosure.

What is claimed is:

1. A method for insufflating a patient cavity with an insufflation fluid, the method comprising:
   determining, by a controller, a first pressure measurement indicative of a pressure of the patient cavity;
   supplying, by an insufflator, the insufflation fluid to the patient cavity based on the first pressure measurement, wherein the insufflation fluid is supplied according to a first setting, the first setting comprising at least a first volume and a first pressure and wherein supplying the insufflation fluid includes directing the insufflation fluid through a first conduit to a bypass valve, the bypass valve comprising at least a first channel and a second channel defining a portion of a first flow path and a first portion of a second flow path, respectively;
   directing the insufflation fluid to the patient cavity via the first flow path when the second channel is closed, wherein the first flow path is further defined by a second conduit coupling the first channel of the bypass valve to a first medical appliance;
   directing the insufflation fluid to the patient cavity via the second flow path when the first channel is closed, wherein the second flow path is further defined by a third conduit coupling the second channel of the bypass valve to a second medical appliance;
   determining, by the controller, that one of the first channel or the second channel is closed;
   in response to determining that one of the first channel or the second channel is closed, subsequently supplying, by the insufflator, the insufflation fluid according to a second setting, wherein:
      the second setting comprises at least a second volume and a second pressure; and
      the second setting is different than the first setting.

2. The method of claim 1, further comprising:
   determining, by a pressure sensor of the first medical appliance, the first pressure measurement.

3. The method of claim 1, further comprising:
   receiving, via one or more cables coupling the first medical appliance to the insufflator, the first pressure measurement determined by a pressure sensor of the first medical appliance.

4. The method of claim 1, further comprising:
   in response to determining that the insufflation fluid is not being supplied to the patient cavity, instructing a pressure sensor of the insufflator to take the first pressure measurement, wherein the first pressure measurement is based on information delivered via the second flow path.

5. The method of claim 1, further comprising:
   subsequent to supplying the insufflation fluid based on the first pressure measurement, supplying the insufflation fluid based on a second pressure measurement determined by a pressure sensor of the first medical appliance.

6. The method of claim 1, further comprising:
   instructing a pressure sensor of the insufflator to take a second pressure measurement in response to determining that the first channel is closed.

7. The method of claim 1, further comprising:
   instructing, by the controller, the bypass valve to close one of the first channel or the second channel in response to determining that the pressure of the patient cavity is at or above a threshold.

8. The method of claim 1, further comprising disabling a pressure sensor when the pressure sensor is not actively measuring pressure.

9. The method of claim 1, further comprising:
   determining, by the insufflator, a change in height of the first medical appliance or the second medical appliance relative to a change in pressure in the patient cavity.

* * * * *